(12) United States Patent
Smith et al.

(10) Patent No.: US 11,439,397 B2
(45) Date of Patent: Sep. 13, 2022

(54) SUTURING APPARATUS AND METHOD

(71) Applicant: GYRUS ACMI, INC., Westborough, MA (US)

(72) Inventors: Adam Lee Smith, Palm Desert, CA (US); Clifton A. Alferness, Olalla, WA (US); Gina M. Muia-Longman, Seattle, WA (US); David R. Seward, Seattle, WA (US); Chenhao Fu, Renton, WA (US); Ilia Timonin, Seattle, WA (US); Blake R. Stancik, Mukilteo, WA (US); Amanda Kay Woodcock, Seattle, WA (US); David A. Desmarais, Seattle, WA (US); Donald C. Baumgarten, Seattle, WA (US); Paul T. Hinrichs, Seattle, WA (US); Thomas H. Ruscher, Seattle, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 83 days.

(21) Appl. No.: 16/367,168

(22) Filed: Mar. 27, 2019

(65) Prior Publication Data
US 2020/0305876 A1  Oct. 1, 2020

(51) Int. Cl.
*A61B 17/11* (2006.01)
*A61B 17/04* (2006.01)
*A61B 17/06* (2006.01)

(52) U.S. Cl.
CPC .......... *A61B 17/11* (2013.01); *A61B 17/0469* (2013.01); *A61B 17/0482* (2013.01); *A61B 17/06* (2013.01); *A61B 2017/1107* (2013.01)

(58) Field of Classification Search
CPC ..... A61B 17/11; A61B 17/0469; A61B 17/06; A61B 17/0482; A61B 2017/1107; A61B 2017/00398; A61B 2017/06076; A61B 2017/1132; A61B 2017/1135;
(Continued)

(56) References Cited

U.S. PATENT DOCUMENTS

| 6,015,416 A * | 1/2000 | Stefanchik ............ A61B 17/11 606/1 |
| 6,514,263 B1 | 2/2003 | Stefanchik et al. |
| 6,530,932 B1 | 3/2003 | Swayze et al. |

(Continued)

OTHER PUBLICATIONS

Assessment of Patented Coronary End-to-Side Anastomotic Devices Using Micromechanical Bonding.

*Primary Examiner* — Sarah A Simpson
(74) *Attorney, Agent, or Firm* — Schwegman Lundberg & Woessner, P.A.

(57) ABSTRACT

Disclosed embodiments include apparatuses, systems, and methods for driving a needle to facilitate suturing, such as may be performed in a surgical anastomosis procedure. In an illustrative embodiment, an apparatus includes a frame. First and second rollers are rotatably mounted parallel with each other in the frame and are configured to engage therebetween a shaft of a needle formed in a helical shape. The first and second rollers are configured to counter-rotate. The needle is revolvable eccentrically around the first roller responsive to counter-rotation of the first and second rollers. A drive mechanism is secured to the frame and is configured to move the frame.

13 Claims, 6 Drawing Sheets

(58) Field of Classification Search
CPC .............. A61B 17/0483; A61B 17/062; A61B 17/0625; A61B 2014/06171; A61B 2014/06076
See application file for complete search history.

(56) References Cited

U.S. PATENT DOCUMENTS

| | | | |
|---|---|---|---|
| 6,613,058 B1* | 9/2003 | Goldin ............... | A61B 17/0469 606/144 |
| 8,906,039 B2* | 12/2014 | Crainich ............ | A61B 17/0469 606/144 |
| 2019/0388087 A1* | 12/2019 | Almodovar ........ | A61B 17/0483 |

* cited by examiner

SUTURING APPARATUS AND METHOD

FIELD

The present disclosure relates to apparatuses, systems, and methods for suturing an object such as a juncture of two passages.

BACKGROUND

The statements in this section merely provide background information related to the present disclosure and may not constitute prior art.

Surgical anastomosis enables segments of one or more arteries, blood vessels, intestines, or any other passages to be connected or reconnected, such as in coronary artery bypass graft (CABG) procedures. In a CABG procedure, for example, a saphenous vein may be harvested from a patient's leg and grafted to circumvent a coronary arterial blockage. Such procedures are tremendously useful and may regularly save and extend lives.

However, CABG procedures and similar procedures involve highly invasive surgery. For example, a typical CABG procedure involves performing a median sternotomy in which a vertical incision is made along the patient's sternum, after which the sternum itself is actually broken open to provide access to the heart and surrounding arteries. The median sternotomy provides a surgeon with space to insert a graft and suture the graft to a coronary artery to complete the process. However, the sizable incision and the breaking of the sternum may involve significant scarring, discomfort, and risk of infection, and may require significant recovery time for the healing of the affected structures.

SUMMARY

Disclosed embodiments include apparatuses, systems, and methods for driving a needle to facilitate suturing, such as may be performed in a surgical anastomosis procedure involving veins, arteries, or other passages.

In an illustrative embodiment, an apparatus includes a frame. First and second rollers are rotatably mounted parallel with each other in the frame and are configured to engage therebetween a shaft of a needle formed in a helical shape. The first and second rollers are configured to counter-rotate. The needle is revolvable eccentrically around the first roller responsive to counter-rotation of the first and second rollers. A drive mechanism is secured to the frame and is configured to move the frame.

In another embodiment, a system includes a needle formed in a helical shape, where the needle includes a shaft having a trailing end configured to draw a filament and a leading end shaped to pierce an object. A drive track is positionable to guide a path of the needle. A needle drive mechanism includes a frame. First and second rollers are rotatably mounted parallel with each other in the frame and are configured to engage therebetween a shaft of a needle formed in a helical shape. The first and second rollers are configured to counter-rotate. The needle is revolvable eccentrically around the first roller responsive to counter-rotation of the first and second rollers. A drive mechanism is secured to the frame and is configured to move the frame along the drive track.

In a further illustrative embodiment, in an illustrative method opposing sides of a shaft of a needle are engaged between parallel faces of first and second rollers, where the needle is formed in a helical shape and configured to draw a filament from its trailing end. The first and second rollers are counter-rotated to cause the helically-shaped needle to revolve eccentrically around the first roller positioned adjacent to an object to cause a leading end of the needle to pierce the object adjacent to an outer face of the first roller. The first and second rollers are translated along an edge of the object. Counter-rotating the first and second rollers and translating the first and second rollers causes the needle to draw the filament to suture the edge of the object adjacent the outer face of the first roller.

Further features, advantages, and areas of applicability will become apparent from the description provided herein. It will be appreciated that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

DETAILED DESCRIPTION

It will be noted that the first digit of three-digit reference numbers corresponds to the figure number in which the element first appears.

The following description explains, by way of illustration only and not of limitation, various embodiments of noninvasive apparatuses, systems, and methods for suturing an object, such as a juncture of passages being joined together in a surgical anastomosis procedure.

Figure 1:
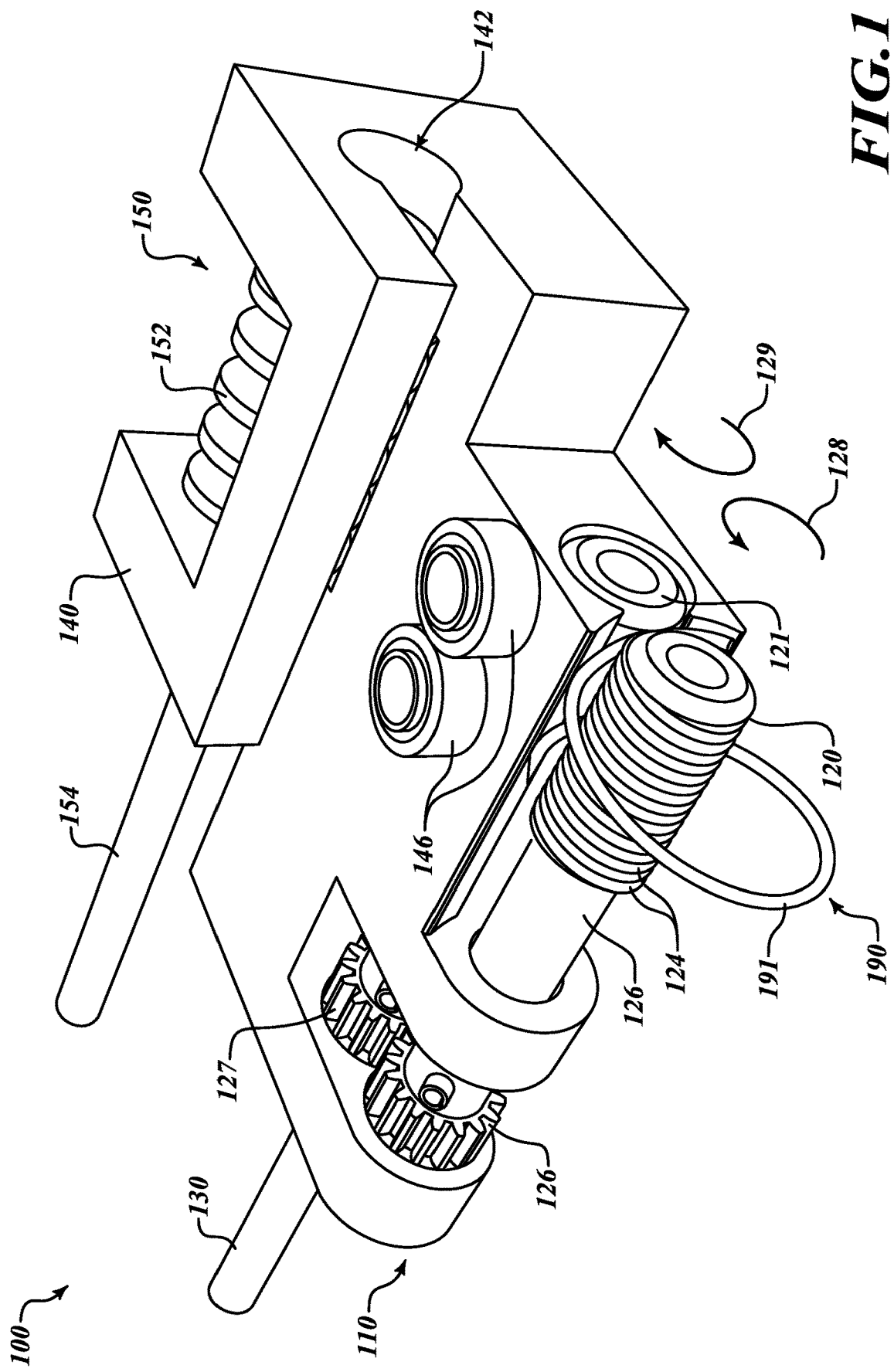
FIG. 1 is a perspective view of an embodiment of an apparatus for suturing an object with a helically-shaped needle.

Given by way of non-limiting overview and referring to FIG. 1, in various embodiments an apparatus 100 includes a frame 110. Rollers 120 and 121 are rotatably mounted parallel with each other in the frame 110 and are configured to engage therebetween a shaft 191 of a needle 190 formed in a helical shape. The rollers 120 and 121 are configured to counter-rotate. The needle 190 is revolvable eccentrically around the roller 120 responsive to counter-rotation of the rollers 120 and 121. A drive mechanism 150 is secured to the frame 110 and is configured to move the frame 110.

Now that an overview has been given, details of various embodiments will be explained by way of non-limiting examples given by way of illustration only and not of limitation.

Still referring to FIG. 1, in various embodiments the apparatus 100 may be well suited for suturing together passages or other objects. In such embodiments the frame 110 is adapted for supporting the rollers 120 and 121. The rollers 120 and 121 are configured to drive the needle 190 to draw a filament to suture one or more objects (not shown in FIG. 1). In the example of a CABG procedure, the objects may include an end of a donor passage and an opening in a receiving passage that may be joined together with sutures to complete an anastomosis procedure. In various embodiments the apparatus 100 is adapted to be compact for insertion into a bodily cavity, for example, by insertion into a patient's chest cavity via a subxiphoid incision made below a sternum of the patient (not shown). It will be appreciated that insertion of the apparatus 100 inserted through a relatively minor incision for use in suturing may help contribute to reducing potential trauma, risk, and protracted healing process that may result from performance of a median sternotomy, as commonly may be used to perform the implantation and suturing of a donor vein in a conventional CABG procedure.

However, it will be appreciated that use of the apparatus 100 is not limited to CABG procedures. Given by way of non-limiting examples, the apparatus 100 may be used for suturing in other procedures, such as without limitation, forming suturing an arteriovenous fistula between an artery and a vein for dialysis, suturing a colostomy formed between the bowel and the skin of the abdominal wall, or in coupling ends of intestinal sections when a formerly intervening portion has been removed. As such, it will be appreciated that no such limitations are intended and are not to be inferred.

In various embodiments, recesses in the frame 110 receive the rollers 120 and 121, as further described below with reference to FIG. 2. The recesses in the frame enable the rollers 120 and 121 to rotate and to be driven by an external source of rotational force. Although only the roller 120 is exposed in FIG. 1, the roller 121 may have a structure similar to that of the roller 120, as described below with reference to FIG. 2. The roller 120 includes a cylinder 122 which defines a number of grooves 124 that are sized and shaped to engage the shaft 191 of the needle 190. Specifically, the grooves 124 are shaped to have a width and cross-sectional shape to at least partially receive the shaft 191 of the needle 190. The grooves 124 also are angled to accommodate a pitch of the needle 190. The width and pitch of the grooves 124 are further described below with reference to FIG. 2. In various embodiments, the cylinder 122 of the roller 120 may also define feature the grooves 124, while the roller 121 may have a generally flat surface or flat and textured surface configured to press the needle 190 into the grooves 124 of the roller 120.

In various embodiments, drive gears 126 and 127 are configured to engage the rollers 120 and 121, respectively. In some embodiments, the drive gears 126 and 127 may be coupled with the rollers 120 and 121, respectively. In some other embodiments, the drive gears 126 and 127 may be integrally formed as part of the rollers 120 and 121, respectively. The drive gears 126 and 127 are interleaved so that rotation of the roller 120 in a first direction causes the roller 121 to counter-rotate in a second, opposite direction. As a result, imparting a rotational force to the roller 121, for example, causes the roller 121 to rotate in a first rotational direction (as indicated by an arrow 128) and cause the roller 120 to counter-rotate in a second rotational direction (as indicated by an arrow 129 that is opposite the first rotational direction). A rotatable member 130, such as a drive shaft or a drive cable, may be directly mechanically coupled to the roller 120 or the roller 121 to provide rotational force to one of the rollers 120 and 121 to cause the rollers 120 and 121 to counter-rotate.

In various embodiments, the needle 190 has a radius larger than that of the roller 120 around which the needle 190 rotates. Thus, when the shaft 191 of the needle 190 is engaged between the rollers 120 and 121, an axis of the needle 190 and an axis of the roller 120 are not colinear. As a result, rotation of the needle 190 (caused by the counter-rotation of the rollers 120 and 121) causes the needle 190 to rotate eccentrically around the roller 120. The eccentric rotation of the needle 190 enables the rollers 120 and 121 to drive the needle 190, thereby causing the needle 190 to repeatedly pierce an object (not shown in FIG. 1) that is adjacent to the roller 120.

In various embodiments, the apparatus 100 may be adapted to follow a drive track (not shown in FIG. 1) that guides the apparatus 100 to operate along a particular course around an object to be sutured (not shown in FIG. 1). In such embodiments, a guide bracket 140 may be disposed on the frame 110. The guide bracket 140 defines an internal guide 142 that is shaped to receive an edge of the drive track so as to hold the frame 110 onto the drive track. The guide bracket 140 also may be configured to receive a drive mechanism 150 and to hold the drive mechanism 150 against the drive track to enable the drive mechanism 150 to motivate the apparatus 100 along the drive track. The frame 110 may include one or more transverse rollers 146 that are configured to rollably engage the drive track to hold the frame 110 to the drive track. The transverse rollers 146 may be mounted on the frame 110 on or adjacent to the guide bracket 140 as shown in FIG. 1.

In various embodiments, the drive mechanism 150 includes a worm gear 152 that is pitched so that rotation of the worm gear 152 moves the apparatus 100 along the drive track. In some embodiments, the worm gear 152 is configured to engage a rotatable drive member 154 that provides rotational force to the worm gear 152. In some other embodiments, the worm gear 152 may be engaged through one or more gears (not shown in FIG. 1) with the rotatable member 130 or one or more of the rollers 120 and 121 to provide rotational force to the worm gear 152.

Figure 2:
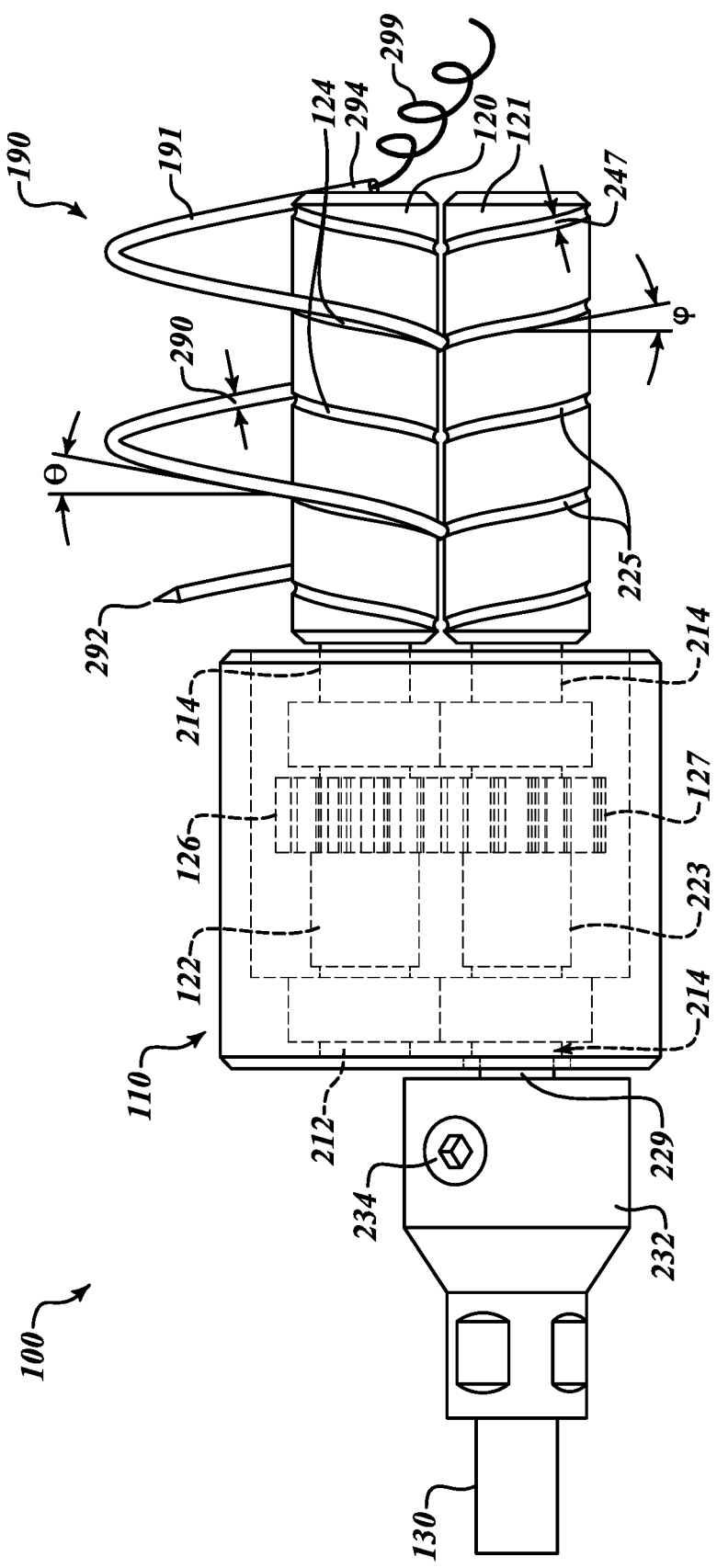
FIG. 2 is a perspective view in partial cutaway form of the apparatus of FIG. 1.

Referring additionally to FIG. 2, in various embodiments both the rollers 120 and 121 include grooves 124 and 225, respectively, to engage the shaft 191 of the needle 190. As shown in FIG. 2, the grooves 124 and 225 are pitched in opposite directions to pinchably and rollably engage the shaft 191 of the needle 190. A width 247 of the grooves 124 and 225 is sized to releasably engage a width 290 of the shaft 191 of the needle 190. A pitch $\varphi$ of the grooves 124 and 225 match a pitch $\theta$ of the needle 190. The corresponding widths 247 and 290 and corresponding pitches $\varphi$ and $\theta$ enable the rollers 120 and 121 to drive eccentric rotation of the needle 190 around the roller 120 as the rollers 120 and 121 counter-rotate. The needle 190 itself includes a leading end 292 that is shaped to pierce an object or objects, such as without limitation tissues that may include edges of donor and receiving passages to be sutured together by the apparatus 100 (FIG. 1). The needle 190 also may include a trailing end 294 configured to receive or to be attached to a filament 299 that is used to suture together the object.

Still referring to FIG. 2, the rollers 120 and 121 include cylinders 122 and 223, respectively, that are rotatably received in the frame 110. At one end, the cylinders 122 and 223 may be rotatably received in cylindrical openings 214 that extend through the frame 110. At an opposing end, each of the cylinders 122 and 223 may be received in a rounded recess 212 or in a cylindrical opening 214. In some embodiments the cylindrical opening 214 may enable a drive shaft 229, that is fixably coupled with the roller 121, to extend through the frame 110. In such embodiments, the drive shaft 229 may thus engage the rotatable member 130, thereby providing rotational force to the roller 121. The rotational force is also provided to the roller 120 via the interleaved drive gears 126 and 127, thereby causing the roller 120 and the roller 121 to counter-rotate. It will be appreciated that, in some other embodiments, the drive shaft 229 may be fixably coupled with the roller 120 such that the interleaved drive gears 126 and 127 impart rotational force to the roller 121, thereby causing the roller 120 and the roller 121 to counter-rotate.

In various embodiments, the rotatable member 130 may be mechanically joined to the drive shaft 229 by a coupling 232 which may be securable and removable by an attachment device 234, such as without limitation an inset screw. The rotatable member 130 may be driven by a motor (not shown in FIG. 2) that is disposed external to the apparatus 100. The cylindrical openings 214 and/or the rounded recess 212 may include bushings (not shown in FIG. 2) formed of nylon or other materials to reduce friction and/or vibration between the rollers 120 and 121 and the frame 110 and/or between the drive shaft 229 and the frame 110.

Figure 3:
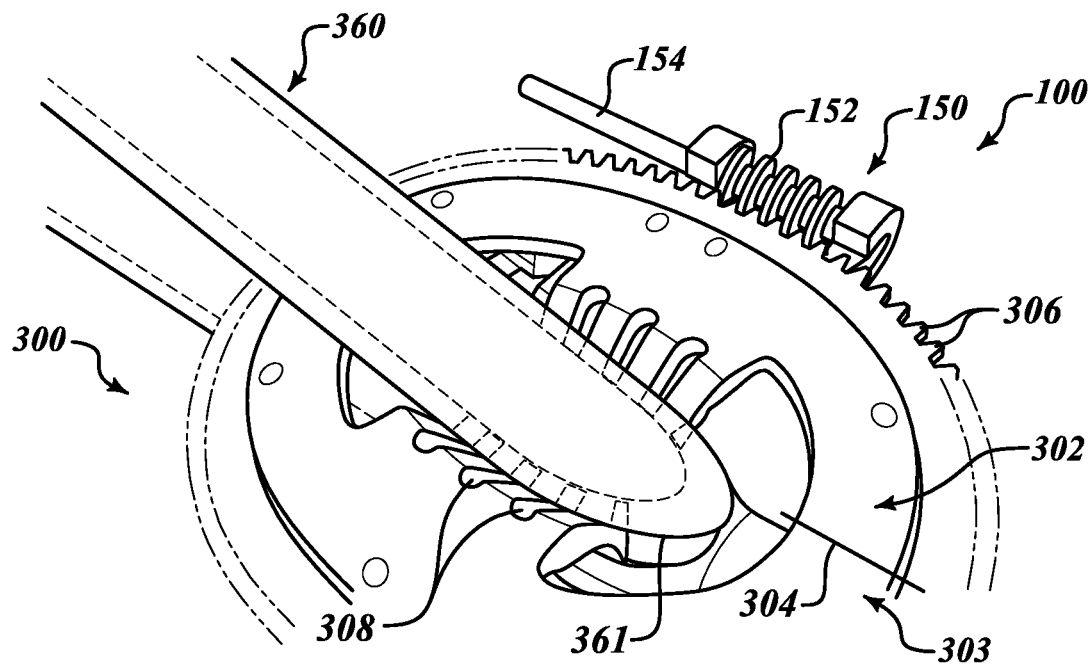
FIGS. 3 and 4 are top and bottom perspective views, respectively, of the apparatus of FIG. 1 positioned on a drive track for guiding the apparatus of FIG. 1.

Referring additionally to FIG. 3, in various embodiments a drive track 300 is used to guide the apparatus (not shown in FIG. 3) around an object to be sutured. FIG. 3 shows a donor passage 360 having a distal edge 361 to be joined to a receiving passage (not shown in FIG. 3) as in an anastomosis procedure. The drive track 300 may include separate sections 302 and 303 that may be positioned around an object, such as the donor passage 360, and then mechanically coupled at a junction 304. The drive track 300 supports teeth 306 that are shaped and sized to be engaged by the worm gear 152. In various embodiments, rotational force imparted by the rotational drive member 154 drives the worm gear 152 and, thus, causes the worm gear 152 to translate the apparatus 100 along the guide track 300. The interaction of the worm gear 152 and the drive track 300 thus causes the apparatus 100 to translate along an edge of the object, such as the distal end 361 of the donor passage 360. In various embodiments the drive track 300 includes inner channels 308 defined along the object that enable the needle (not shown in FIG. 3) to extend from the apparatus 100 to and through the object.

Figure 4:
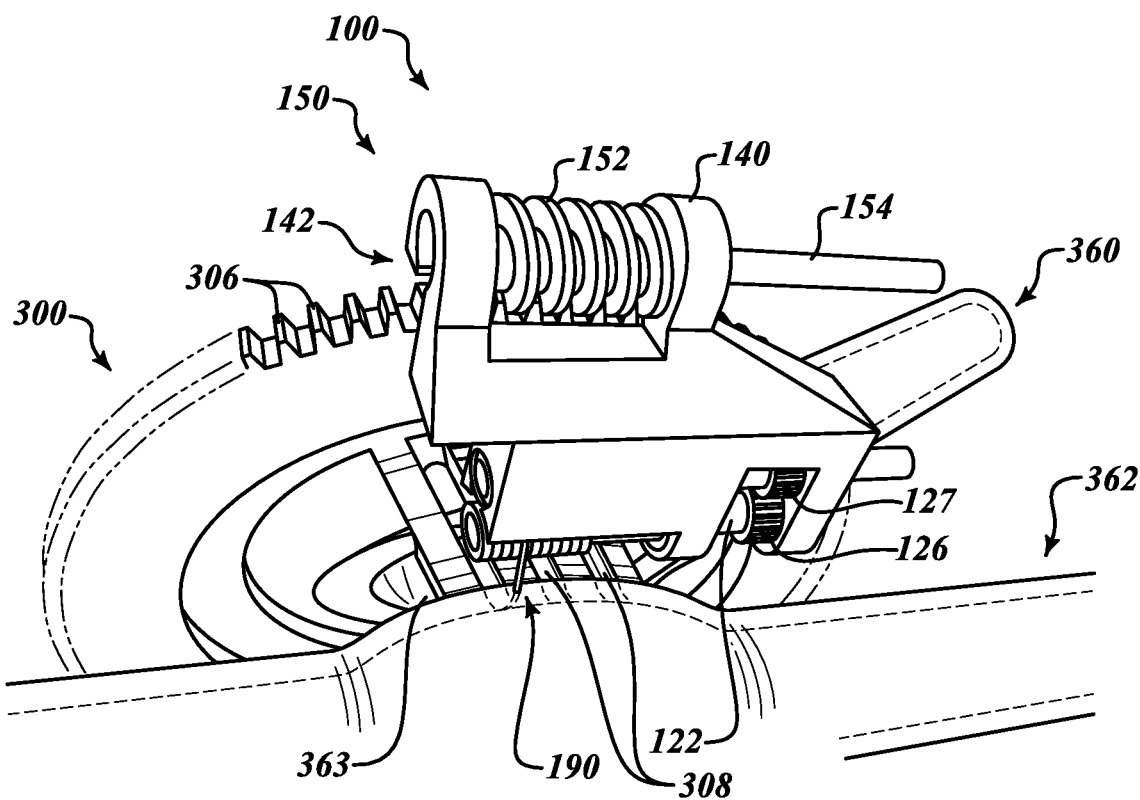

Referring additionally to FIG. 4, the guide bracket 140 of the frame 110 guides the apparatus 100 along the drive track 300. The receiving passage 362 defines an opening 363 beneath the drive track 300. The guide bracket 140 engages the drive track 300, and the drive track 300 is received in the internal guide 142 defined by the guide bracket 140. As previously described, the guide bracket 140 holds the worm gear 152 against the teeth 306 of the drive track 300. As a result, rotational force imparted to the worm gear 152 by the rotational drive member 154 causes the worm gear 152 to move the apparatus 100 around the drive track as the needle 190 passes through the channels 308 in the drive track 300 to suture the object.

Figure 5:
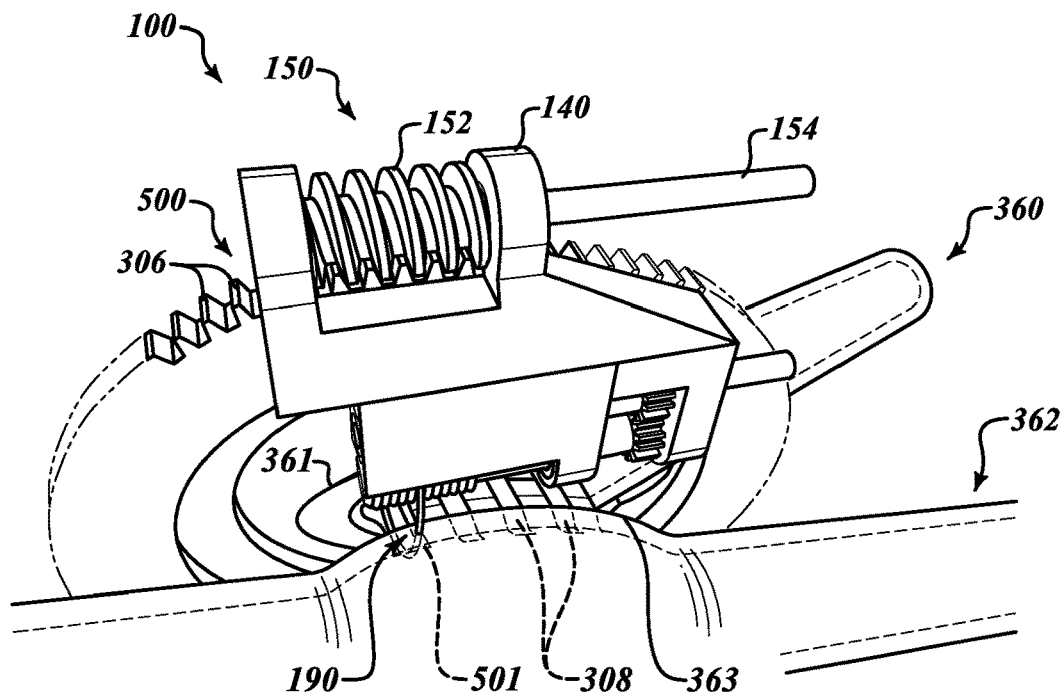
FIGS. 5 and 6 are views of the apparatus of FIG. 1 at different locations along the guide track of FIGS. 3 and 4 to illustrate a process of suturing using the apparatus of FIG. 1.
Figure 6:
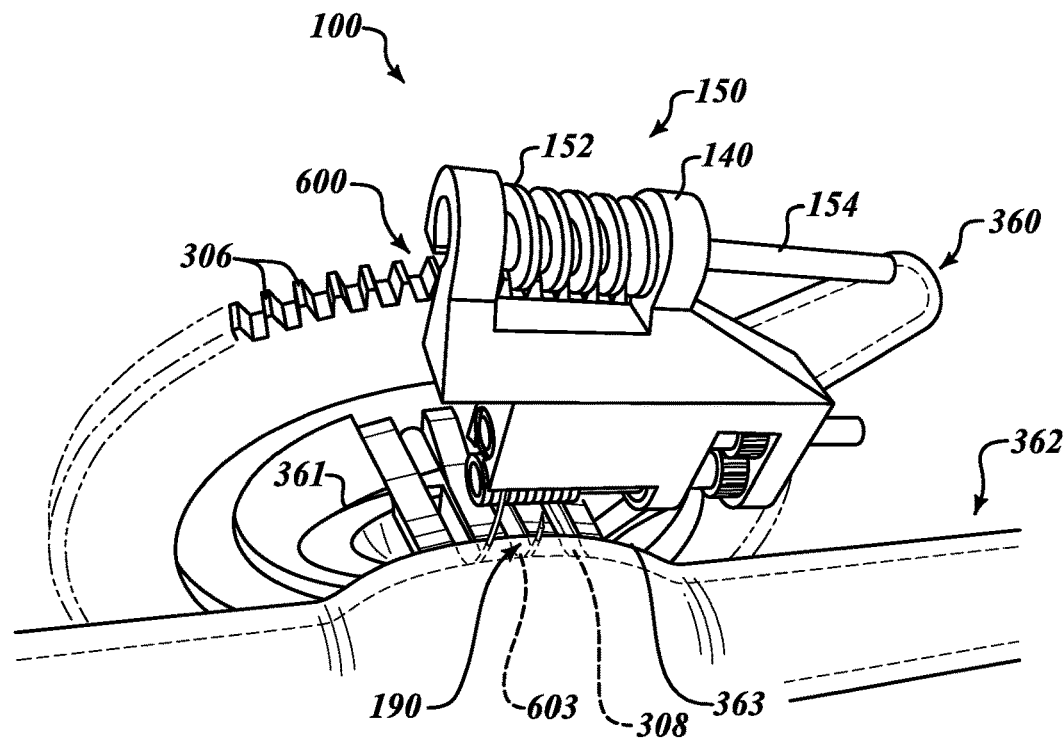

Referring additionally to FIGS. 5 and 6, the apparatus 100 moves around the drive track 300 as the needle 190 is rotated to suture the object. As shown in FIG. 5, the apparatus 100 is situated at a first point 500 along the drive track 300, and the needle 190 extends through a first channel 501 in the drive track 300. As shown in FIG. 6, rotation of the worm gear 152 has moved the apparatus 100 along the guide track 300 to a second point 600 while the needle 190 has been rotated. As a result, the needle 190 now extends through a second channel 603 in the drive track 300. The motion of the apparatus 100 around the guide track 300 as the needle 190 is rotated through an object thus sutures the object (which in this non-limiting example is a juncture of the donor passage 360 and the receiving passage 362).

It will be appreciated that, as shown in FIGS. 3-6, the drive track 300 suitably is a rounded track configured to lead the apparatus 100 around an object to suture the object, for example, to join passages together. However, it will be appreciated that a linear drive track may be used to form a linear suture, for example, to close a wound or incision. Thus, it will be appreciated that disclosed embodiments are not intended to be limited to a drive track 300 of any particular shape or size and no such limitation is to be inferred.

Figure 7:
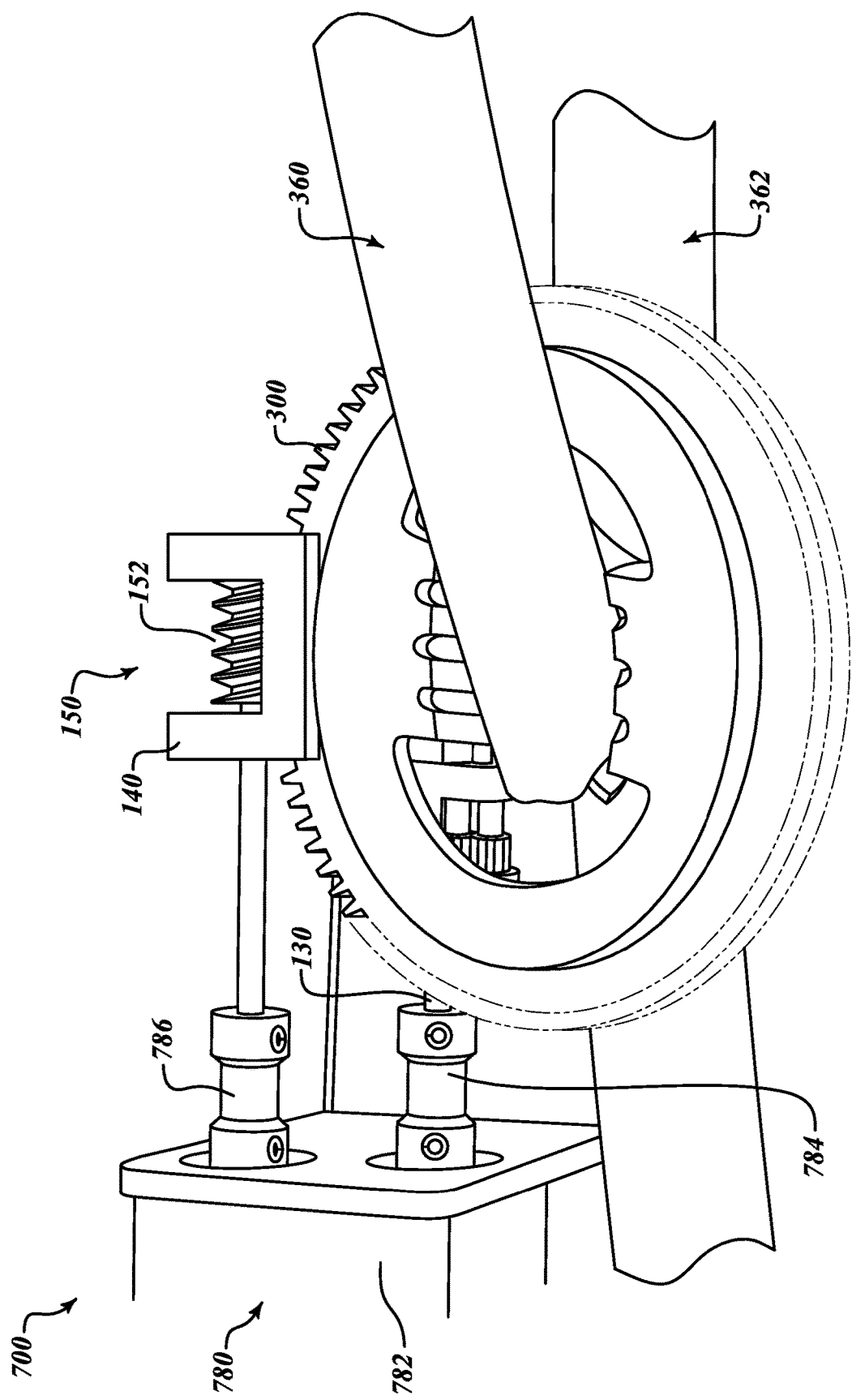
FIG. 7 is a perspective view of a system having a motor to impart rotational force to the apparatus of FIG. 1.

Referring additionally to FIG. 7 and in various embodiments, in an illustrative system 700 the drive track 300 is positioned around the object or objects to be sutured. A motor 780 provides rotational force to rotate the rollers 120 and 121 (not shown in FIG. 7) and to drive the worm gear 152. In various embodiments, a single motor 780 or multiple motors (not shown) may be used to provide rotational force to the rollers 120 and 121 and the worm gear 152 of the drive mechanism 150. The motor 780 may include a gear box 782 so that, as desired, the single motor 780 may provide rotational force at different speeds to the rotational member 130 that is coupled with the rollers 120 and 121 and the rotational drive member 154 that is coupled to the worm gear 152 of the drive mechanism 150. The system 700 may include drive linkages 784 and 786 to connect with the rotational member 130 and the rotational drive member 154. The drive linkages 784 and 786 may include flexible drive cables to provide rotational force while accommodating motion and positioning of the apparatus 100.

In various embodiments and as shown in FIG. 7, the gear box 782 may be positioned at or adjacent to the motor 780 with multiple drive linkages 784 and 786 extending to the rollers 120 and 121 and to the drive mechanism 150. In some other embodiments, the gear box 782 may be positioned at the apparatus 100 so that rotational force imparted to one of the rollers 120 and 121 may be mechanically conveyed to the drive mechanism 150 or vice versa. As a result, with only a single linkage extending from the motor 780 to the apparatus, in such embodiments rotational force may be provided to both the rollers 120 and 121 and to the drive mechanism 150.

Figure 8:
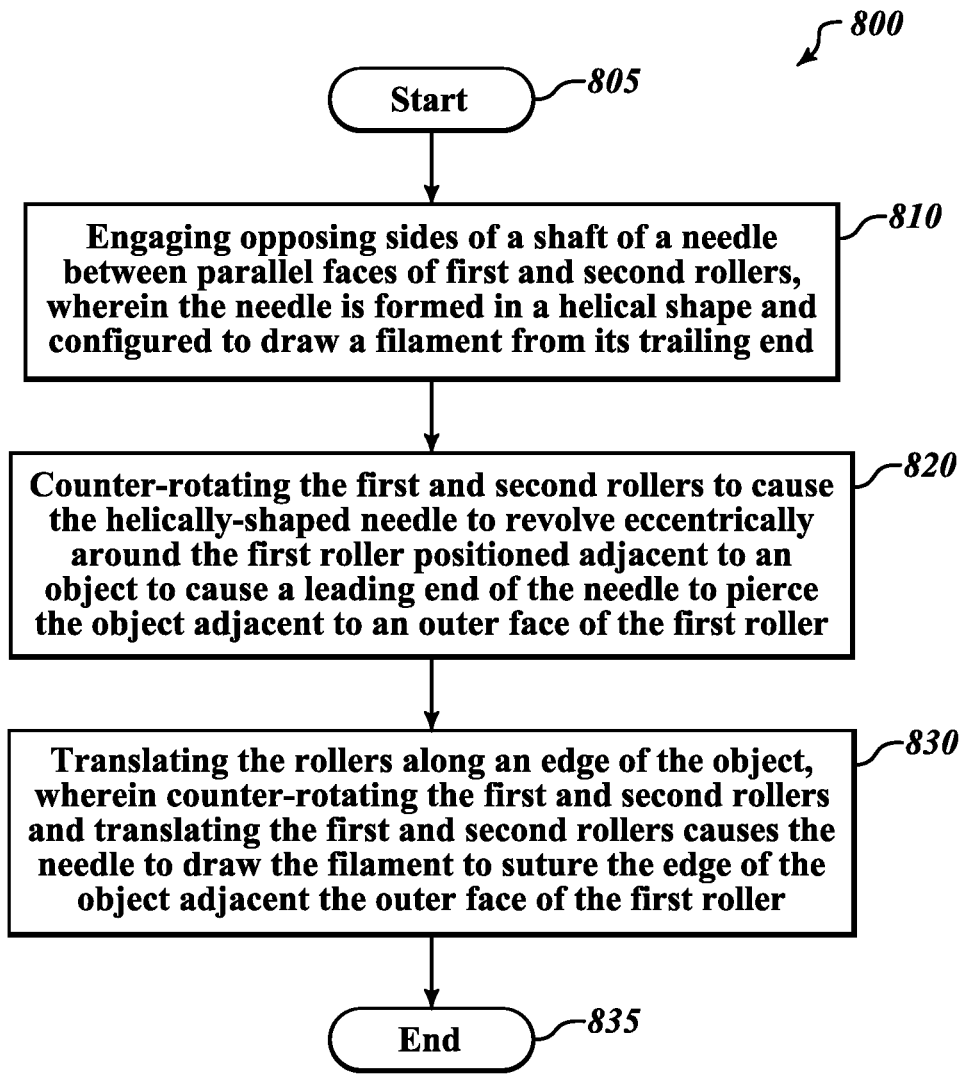
FIG. 8 is a flow diagram of an illustrative method of suturing an object.

Referring additionally to FIG. 8, in various embodiments an illustrative method 800 of suturing an object, such as in an anastomosis, is provided. The method 800 starts at a block 805. At a block 810, opposing sides of a shaft of a needle are engaged between parallel faces of first and second rollers, where the needle is formed in a helical shape and is configured to draw a filament from its trailing end. At a block 820, the first and second rollers are counter-rotated to cause the helically-shaped needle to revolve eccentrically around the first roller that is positioned adjacent to an object. Counter-rotation of the first and second rollers causes a leading end of the needle to pierce the object adjacent to an outer face of the first roller. At a block 830, the first and second rollers are translated along an edge of the object. Counter-rotating the first and second rollers and translating the first and second rollers causes the needle to draw the filament to suture the edge of the object adjacent the outer face of the first roller. With the object sutured, the method 800 ends at a block 835.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
   a frame;
   a needle having a shaft formed in a helical shape, the shaft configured to draw a filament from an end thereof;
   a first roller and a second roller rotatably mounted parallel with each other in the frame and configured to engage therebetween the shaft of the needle, the needle disposed around the first roller, wherein a radius of the needle is greater than a radius of the first roller and an axis of needle is noncolinear with an axis of the first roller, the first roller and the second roller being configured to counter-rotate, the needle being revolvable eccentrically around the first roller responsive to counter-rotation of the first roller and the second roller; and
   a drive mechanism secured to the frame and configured to move the frame to translate the first roller and the second roller and the needle relative to an object as the first roller and the second roller are counter-rotated to revolve the needle through the object to form a suture.

2. The apparatus of claim 1, wherein faces of at least one of the first roller and the second roller defines angled grooves that are sized to at least partially receive the shaft of the needle and that are angled to align with a pitch of the helical shape of the needle.

3. The apparatus of claim 1, further comprising:
   a first drive gear configured to engage the first roller; and
   a second drive gear configured to engage the second roller, the first drive gear and the second drive gear being further configured to cooperate with each other such that the first roller is rotatable in a first rotational direction and the second roller is counter-rotatable in a second rotational direction that is opposite the first rotational direction.

4. The apparatus of claim 3, further comprising a roller drive shaft configured to receive a rotatable member that is configured to provide rotational force to cause the first roller and the second roller to counter-rotate.

5. The apparatus of claim 1, wherein the drive mechanism includes:
   a worm gear rotatably received in the frame and configured to engage a drive track; and
   a guide bracket disposed on the frame and configured to support the worm gear in engagement with the drive track, the frame being motivatable along the drive track responsive to rotation of the worm gear.

6. The apparatus of claim 5, further comprising at least one transverse roller mounted on the frame and configured to rollingly engage the drive track to maintain the guide bracket in position to hold the worm gear against the drive track.

7. The apparatus of claim 5, wherein the drive mechanism is further configured to cause the worm gear to rotate by a causality chosen from: mechanically engaging at least one of the first roller and the second roller so that rotation of the at least one of the first roller and the second roller causes the worm gear to rotate and receiving a rotatable drive member configured to provide rotational force to cause the worm gear to rotate.

8. A system comprising:
   a needle formed in a helical shape, wherein the needle includes a shaft having a trailing end configured to draw a filament and a leading end shaped to pierce an object;
   a drive track that is positionable to guide a path of the needle; and
   a needle drive mechanism including:
      a frame;
      a first roller and a second roller rotatably mounted parallel with each other in the frame and configured to engage therebetween the shaft of the needle, the first roller and the second roller being configured to counter-rotate, the needle being revolvable eccentrically around the first roller responsive to counter-rotation of the first roller and the second roller; and
      a drive mechanism secured to the frame and configured to move the frame along the drive track, wherein the drive mechanism includes:
         a worm gear rotatably received in the frame and configured to engage the drive track; and
         a guide bracket disposed on the frame and configured to support the worm gear in engagement with the drive track, the frame being motivatable along the drive track responsive to rotation of the worm gear.

9. The system of claim 8, wherein faces of at least one of the first roller and the second roller defines angled grooves that are sized to at least partially receive the shaft of the needle and that are angled to align with a pitch of the helical shape of the needle.

10. The system of claim 8, further comprising:
    a first drive gear configured to engage the first roller; and
    a second drive gear configured to engage the second roller, the first drive gear and the second drive gear being further configured to cooperate with each other such that the first roller is rotatable in a first rotational direction and the second roller is counter-rotatable in a second rotational direction that is opposite the first rotational direction.

11. The system of claim 10, further comprising a roller drive shaft configured to receive a rotatable member that is configured to provide rotational force to cause the first roller and the second roller to counter-rotate.

12. The system of claim 8, further comprising at least one transverse roller mounted on the frame and configured to rollingly engage the drive track to maintain the guide bracket in position to hold the worm gear against the drive track.

13. The system of claim 8, wherein the drive mechanism is further configured to cause the worm gear to rotate by a causality chosen from: mechanically engaging at least one of the first roller and the second roller so that rotation of the at least one of the first roller and the second roller causes the worm gear to rotate and receiving a rotatable drive member configured to provide rotational force to cause the worm gear to rotate.

* * * * *